United States Patent [19]

Foster et al.

[11] Patent Number: 4,644,076
[45] Date of Patent: Feb. 17, 1987

[54] CONTINUOUS PROCESS FOR THE SYNTHESIS OF HEXAMETHYLDISILAZANE

[75] Inventors: Roland S. Foster, Melbourne Beach; Craig A. Ellis, Palm Bay, both of Fla.

[73] Assignee: FAR Research, Inc., Melbourne, Fla.

[21] Appl. No.: 722,276

[22] Filed: Apr. 11, 1985

[51] Int. Cl.$^4$ ............................................. C07F 7/10
[52] U.S. Cl. .................................................. 556/412
[58] Field of Search ........................................ 556/412

[56] References Cited

U.S. PATENT DOCUMENTS 3,809,713  5/1974  Boersma et al. .................... 556/412
3,927,057  12/1975  Takamizawa et al. .......... 556/412 X

FOREIGN PATENT DOCUMENTS 2834027  2/1980  Fed. Rep. of Germany ...... 556/412

*Primary Examiner*—Paul F. Shaver
*Attorney, Agent, or Firm*—Porter, Wright, Morris & Arthur

[57] ABSTRACT

A continuous process for the production of hexamethyldisilazane consisting of introducing predetermined quantities of trimethylcholorosilane and gaseous ammonia to form a mixture of hexamethyldisilazane and ammonium chloride in a first reactor, while simultaneously subjecting said mixture to continuous high shear agitation to form a slurry, and then separating the ammonia choloride from said slurry to provide a solution principally comprising hexamethyldisilazane and apparatus useful with the foregoing process.

7 Claims, 2 Drawing Figures

CONTINUOUS PROCESS FOR THE SYNTHESIS OF HEXAMETHYLDISILAZANE

FIELD OF THE INVENTION

This invention relates to a process for the manufacture of hexamethyldisilazane (HMDS) and apparatus useful and by-products produced in conjunction therewith.

BACKGROUND OF THE INVENTION

Hexamethyldisilazane (HMDS) has well known utility in many industrial operations. The equations for the synthesis of HMDS are well known in the prior art and the production of HMDS in a bulk process using stoiciometric quantities of the intermediates trimethylsilyl chloride (trimethyl chlorosilane or "TMCS") and ammonia in a solvent medium is a standard process.

OBJECT AND SUMMARY OF THE INVENTION

It is an object of the invention herein to provide a continuous process to produce hexamethyldisilazane (HMDS) in large quantities and in a highly purified form. In this connection, is an object to provide an apparatus useful in the continuous production of HMDS which consists of a first continuous flow reactor which is followed by a centrifuge which removes the by-product ammonium chloride that is produced in the HMDS synthesis reaction. In the process and apparatus, the crude HMDS obtained as filtrate from the centrifuge is then treated with sodium amide so that impurities are removable by subsequent steps of filtration and/or fractional distillation. In this manner it is an object of the present invention to produce high purity (99 plus %) HMDS in large quantities in a continuous process in a single distillation.

BRIEF DESCRIPTION OF THE DRAWINGS

These objects of the invention will become apparent when the following description of the preferred embodiment is taken in conjunction with the drawings in which.

DESCRIPTION OF THE PREFERRED EMBODIMENT

Figure 1:
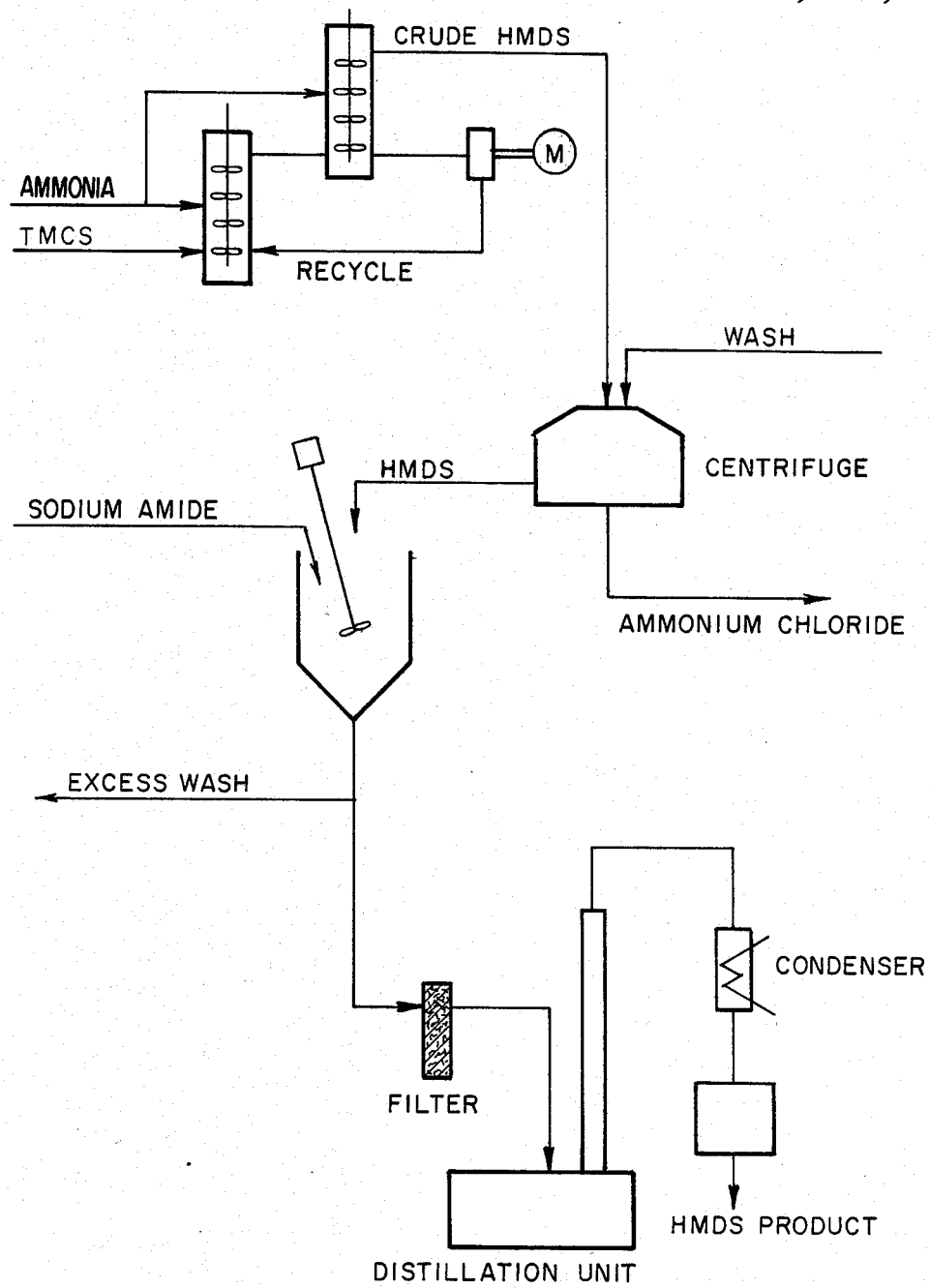
FIG. 1 is a overall flow chart for the continuous process for the synthesis of HMDS.

In a summary of the process shown in FIG. 1, liquid trimethylchlorosilane (TMCS) and gaseous ammonia are fed to the first of a set of two or more reactors where they combine to form "crude" HMDS and an ammonium chloride by-product slurry. As set forth below, the first stage of the set of two or more reactors is a high shear vessel in which the TMCS and ammonia mixture is subjected to continuous high shear agitation in a recirculating reactor loop. Ammonium chloride produced as a by-product is in a "prilled" form in the resultant slurry. The slurry is then optionally fed to a second high shear reactor to insure that a complete reaction of all TMCS occurs. Then, the slurry is passed to a centrifuge where the ammonium chloride crystals are removed. In the centrifuge, HMDS is removed from the solid ammonium chloride particles in the centrifuge cake by displacement of the HMDS with a non-reactive wash. Suitable washes may be hydrocarbons or a buffered saturated ammonium chloride water solution. The HMDS liquid filtrate passes on to a mix tank where solid sodium amide is added.

The amide is stirred in the crude HMDS until ammonia gas evolution subsides. Excess amide is removed by filtration and the filtrate passes on to the batch still for distillation. Non-volatile amide reaction products are removed with still bottoms. Pure HMDS is distilled overhead.

Table I shows the results of a typical process run producing HMDS in a process following the sequential steps of FIG. 1 with respect to the feedstock intermediates stated.

TABLE I

| A. Reactor Stage | |
|---|---|
| TMCS feed | 1308 lbs. |
| Ammonia used | 307 lbs. |
| Diluent used | 121 lbs. |
| Crude slurry produced | 1691 lbs. |
| B. Purification Stage | |
| Crude HMDS filtrate after amide treatment | 1145 lbs. |
| Distilled product not including recoverable recycle cuts | 767 lbs. |
| C. Yield | |
| Average yield not including recycleable material | 80.4% |

Figure 2:
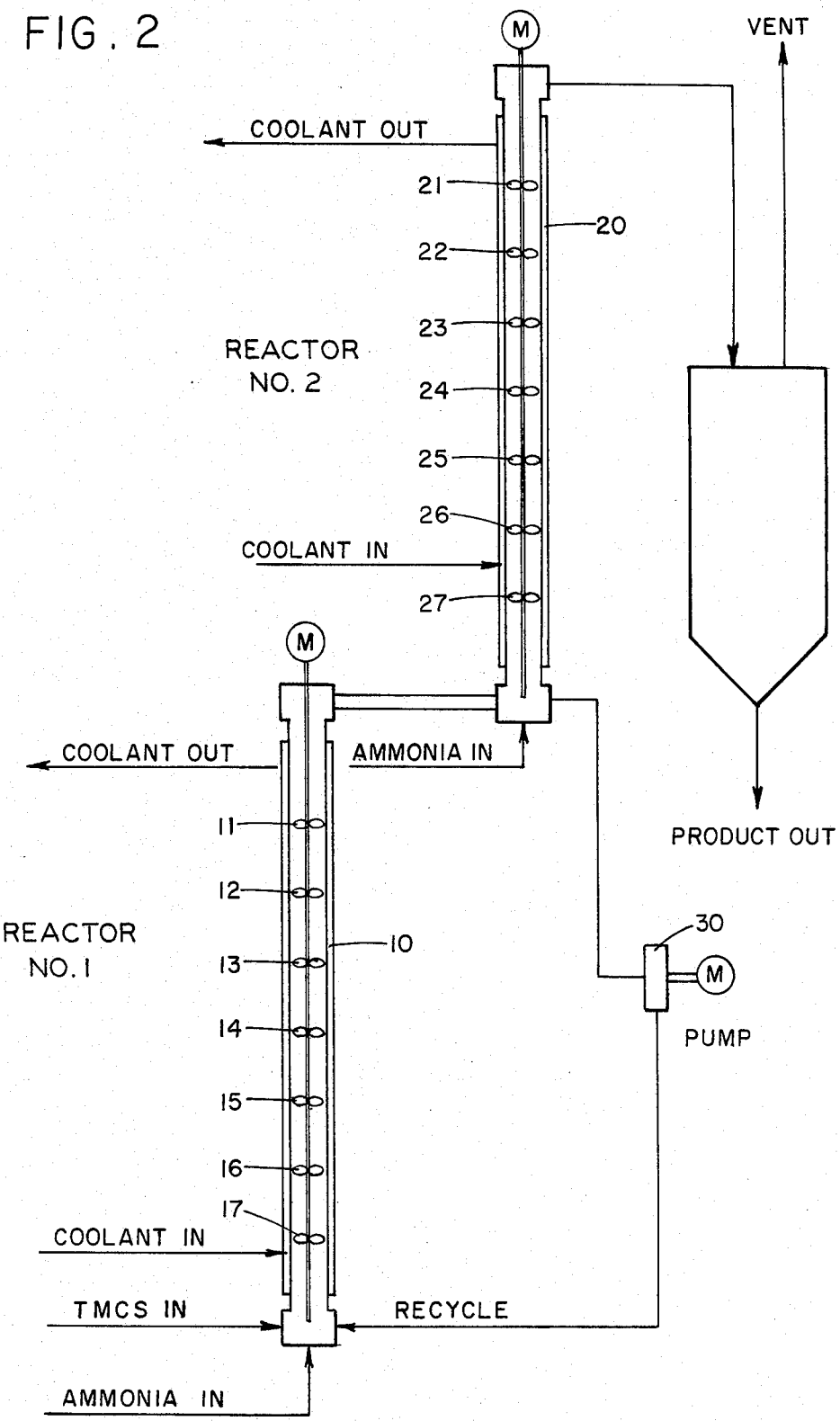
FIG. 2 is a detail of a reactor system used in the process.

FIG. 2 shows in detail a reactor configuration used in the process first stage.

The first stage reactor consists essentially of two separate reactor sections 10 and 20 coupled in series. The liquid TMCS and ammonia gas intermediates are introduced first through the unit section 10 and then through the section 20. Preferably ammonia is introduced in a stoiciometric excess. A pump 30, while transporting a quantity of the fluid to the second reactor section 20, also recirculates the reacting fluid through the first reactor section 10. External heat exchangers can be incorporated in the circulation loop as well as on the body of the reactor vessels to insure that a controlled reaction temperature is maintained. The first and second reactor sections have a high length to diameter ratio to assure high shear and intimate and prolonged gas-liquid contact between the reacting intermediates. One useful L/D (length to diameter) ratio is 15:1 however an appropriate range of L/D ratios is from approximately 5 to 1 to up to about 20 to 1 so that high velocity shear mixing of the liquid TMCS and gas ammonia can be obtained in accordance with the principle of the invention.

In the embodiment shown, each reactor section is agitated with multiple impellers spaced apart and provided in a configuration to disperse the ammonia gas into the reactant fluid and to impart a very high fluid shear to the reacting mixture therein. Thus, paddle, vane, or turbine impellers may be provided; the impellers, to provide a high degree of agitation, are rotated at speeds which produce a tip velocity of the impeller of about between 1,000 and 1,500 feet per minute, for example, for an impeller approximately 3 inches in diameter.

In the first reactor vessel the pump 30 provides a recirculation or recycle in a loop configuration through the first stage. Material transport in the loop is approximately 150 gallons of reactant for each gallon of "new" TMCS fed to the reactor inlet. The residence time of the reactant mixture in the first reactor stage is of a duration of from approximately 10 to about 40 minutes.

As further shown in FIG. 2, additional ammonia is introduced into the second reactor vessel. This addition insures that any TMCS not reacted in the first vessel is contacted with ammonia in the second section so that an essentially complete reaction of all the trimethylchlorosilane (TMCS) intermediate originally introduced occurs.

At a reaction temperature of approximately 50° C. (considered "normal" for the present process) and under the high shear flow conditions set forth in the foregoing description, the consistency of the reacted slurry is observed to be similar to that of milk or light cream, i.e. very fluid. Ammonium chloride particles produced in the reactor settle very rapidly and a clear layer of HMDS appears above a sediment. However, on standing and cooling the slurry consistency changes rapidly to that of a thick milkshake. The consistency varies depending on the presence and amount of any diluent used in the reaction; diluent in the proportion of from about 20% to 30% is required to alter the viscosity of the reaction product on standing.

This observation is of significance because in conventional batch methods for the production of HMDS, the addition of diluent is necessary to reduce the viscosity of the reactant mixture; without the addition of diluent, the consistency of the reactants would approach that of putty; heat transfer would be very slow; and the reaction would not be completed in a reasonable time.

In contrast, the physical state of the ammonium chloride particles produced in the reactor herein differs from that encountered in a conventional batch reaction. In the process herein, the ammonium chloride by-product produced in the reactor consists of "prilled" particles which resemble small spheroid grains of sand. When ammonium chloride particles of that size and shape are dispersed in HMDS, there is little effect on the viscosity of the resulting slurry. Thus, even at high concentrations of ammonium chloride the reactant slurry does not become increasingly viscous. Hence, an advantage of the present process is that HMDS is produced in continuous flow equipment without the use of a diluent or other non-reactant fluid media. In general, it appears that the size and shape of the by product ammonium chloride crystals produced concurrently with the synthesis reaction producing HMDS is determined by the conditions of reaction. In the instant process, relatively large, essentially spherical and mostly unagglomerated ammonium chloride particles are formed in the very high shear, recirculating loop reactor. This occurs when residence time of the reactant mixture in a reactor of type described herein is in the range of 10 to 40 minutes at a controlled temperature range of 40° C. to 60° C. Higher temperatures may be employed at elevated reactor pressures.

Particle size distribution of ammonium chloride particles thus formed is set forth in Table II:

TABLE II

| Ammonium Chloride By Product Particle Size Distribution | |
|---|---|
| % larger than ... | Standard Mesh Size |
| 1.4 | 30 |
| 2.1 | 60 |
| 13.1 | 120 |
| 68.3 | 230 |

Although a specific reactor design providing high shear and a recirculation loop to provide the necessary residence time at a controlled temperature is described herein, it may be noted that such a preferred reactor for use with the present invention will provide: (1) rapid dispersion of the ammonia gas into the reaction liquid; (2) efficient heat transfer to the reactor cooling jackets; (3) effective ammonium chloride dispersion to prevent agglomerate formation; (4) effective suspension of solid particles in the liquid steam; and (5) facilitates production of nearly round ammonium chloride particles.

Table III sets forth a typical set of operating parameters encountered in a reactor having a capacity of 3 gallons, a 4 foot length, a 3 inch internal diameter and seven (7) impellers at approximately 6 inch spacing operating at about between 1400 to 2000 rpm, intended to provide a reactant residence time of from 10 to 40 minutes at a controlled temperature of 50° C.

TABLE III

| Reactor Operating Parameters | |
|---|---|
| Parameter | Measurement |
| Run time | 6 hours |
| TMCS feed | 468 lbs. |
| Average feed rate | 1.3 lbs./min. |
| Diluent | 5% |
| Diluent composition (hydrocarbons) | B.P. range 315 to 390° F. |
| Reactor temperature | |
| (average) | 52° C. |
| (high) | 55 |
| (low) | 45 |
| Circulation pump pressure | 20 PSI |
| Average liquid composition of discharged crude product steam | 94.5% HMDS<br>0.2% TMCS<br>5.0% diluent |
| Weight of crude HMDS produced including ammonium chloride | 574 lbs. |

As is set forth in the overall process flow chart described in FIG. 1, after the reactor stage, the slurry is centrifuged (for example in a perforated basket centrifuge) to recover a HMDS filtrate which is thereafter treated in a final purification step by the addition of sodium amide and distillation.

The chemistry of the final HMDS filtrate treatment step is complex. The reactions occurring in the final amide treatment and distillation steps are, however, not fully understood. Thus, the following description should be understood as presently incomplete and partly hypothetical. In liquid anhydrous ammonia, sodium amide reacts rapidly with ammonium chloride to form ammonia and sodium chloride according to the formula:

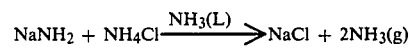

This reaction proceeds slowly, if at all, in HMDS. The ammonium chloride appears to react with a reaction product formed when crude HMDS is "treated" with sodium amide. In this regard, literature reports that sodium bis(trimethylsilyl)amide is formed from the reaction of sodium amide and HMDS in benzene as follows:

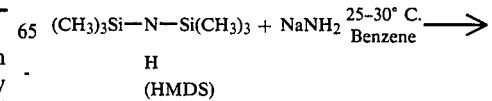

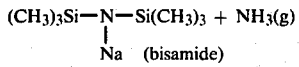

This reaction proceeds moderately at 25°-30° C. with evolution of ammonia without benzene as a solvent.

HMDS in contact with moisture hydrolyzes first to trimethyl silanol (TMSOH) which subsequently condenses to hexamethyldisiloxane (HMDSO) and water by this reaction:

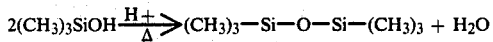

Water produced in this reaction is then available to hydrolyze more HMDS. It is essential to remove trimethylsilanol from the process steam prior to distillation. This is also accomplished by sodium amide. Sodium amide reacts rapidly with TMSOH at ambient temperature as shown:

Trimethylsilanolate formed in this reaction reacts further as shown later.

By product hexamethyldisiloxane in ethyl ether reacts with sodium amide to form sodium trimethylsilanolate and HMDS as follows:

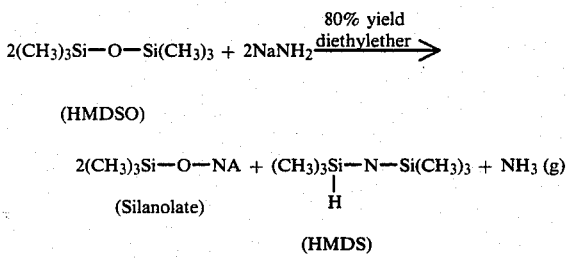

This reaction proceeds slowly without diethylether but reacts faster at reflux temperatures. Trimethylsilanol is condensed during the HMDS distillation step to give HMDSO, which reacts as shown above.

Both of the above reaction products, sodium(bistrimethylsily)amide and sodium trimethylsilanolate react rapidly with TMCS, as reported:

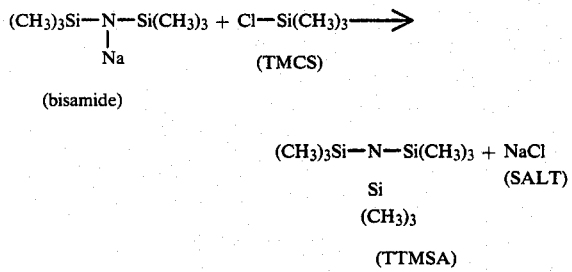

(B) silanolate reaction

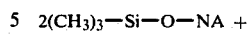

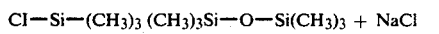

The TTMSA or tris(trimethylsily)amine would be volatile but may decompose to HMDS during distillation and the TMCS is rapidly consumed by either compound. Any residual HMDSO is separated by distillation from the product HMDS.

Overall, the amide treatment results in the removal of unreacted TMCS, reduces the amount of TMSOH and HMDSO present, and renders the ammonium chloride non-volatile. These reactions begin during the amide addition step but are not completed until the distillation step. Product HMDS is formed from HMDSO thereby a high purity HMDS is provided. These reactions should all operate as well or better with potassium or lithium amide but the latter compounds are more expensive than sodium amide.

What is claimed is:

1. A continuous process for the production of hexamethyldisilazane consisting of the concurrent actions of continuously introducing predetermined quantities per time unit of trimethylchlorosilane and gaseous ammonia to form a mixture of hexamethyldisilazane and ammonium chloride in a first reactor while simultaneously subjecting said mixture to continuous high shear agitation, for a time period related to the volume of the reactor and the quantities of trimethylchlorosilane and ammonia introduced, to form a slurry; and simultaneously separating the ammonium chloride from said slurry to provide a solution principally comprising hexamethyldisilazane, while continuing to introduce a continuous flow of further quantities of trimethylchlorosilane and ammonia as the hexamethyldisilazane is removed.

2. The process of claim 1 in which the hexamethyldisilazane separated from the slurry is simultaneously treated with sodium amide and continually filtered and distilled.

3. The process of claim 1 in which the high shear agitation occurs in a continuous recirculating loop reactor having a length to diameter ratio of from about 5 to 1 to about 20 to 1.

4. The process of claim 3 in which residence time of the mixture in the reactor is from about 10 to about 40 minutes and material transport in the recirculating loop is approximately 150 gallons of reactant for each gallon of trimethylchlorosilane introduced in the first reactor.

5. The process of claim 1 in which a minor proportion of a diluent hydrocarbon is introduced into the first reactor mixture of trimethylchlorosilane and ammonia.

6. The process of claim 1 in which the ammonium chloride separated from the slurry is in the form of a mass of prilled particles.

7. The process of claim 1 in which the ammonia is introduced to the first reactor in a stoichiometric excess.

* * * * *